United States Patent [19]

Nakamura et al.

[11] Patent Number: 5,599,104
[45] Date of Patent: Feb. 4, 1997

[54] THERMAL ANALYSIS INSTRUMENT

[75] Inventors: Nobutaka Nakamura; Yoshihiko Teramoto, both of Tokyo, Japan

[73] Assignee: Seiko Instruments Inc., Tokyo, Japan

[21] Appl. No.: 311,739

[22] Filed: Sep. 23, 1994

[30]     Foreign Application Priority Data

Sep. 24, 1993 [JP] Japan .................................. 5-238408

[51] Int. Cl.$^6$ .......................... G01N 25/00; G01N 25/20
[52] U.S. Cl. ................................. 374/12; 374/11
[58] Field of Search .................. 374/10, 11, 12, 374/13, 31

[56]               References Cited

U.S. PATENT DOCUMENTS

| 3,238,775 | 3/1966  | Watts .          |        |
|-----------|---------|------------------|--------|
| 3,537,294 | 11/1970 | Stone            | 374/13 |
| 4,095,453 | 6/1978  | Woo              | 374/13 |
| 5,098,196 | 3/1992  | O'Neill          | 374/11 |
| 5,211,477 | 5/1993  | Li               | 374/10 |
| 5,224,775 | 7/1993  | Reading et al.   | 374/11 |

FOREIGN PATENT DOCUMENTS 1411252 8/1964 France .
2117808 4/1971 Germany .

OTHER PUBLICATIONS

JJGM van Bokhoven, et al., "Fourier analysis for correction of thermograms obtained with a heat flow microcalorimeter of high stability", Journal of physics E scientific instruments, vol. 9 No. 2, Feb. 1976.

Primary Examiner—Diego F. F. Gutierrez
Attorney, Agent, or Firm—Loeb & Loeb LLP

[57]                 ABSTRACT

The temperature of a heat reservoir is varied according to a linear function which is AC modulated. At this time, the temperature difference between two points located in a heat flow path going from the heat reservoir to an unknown sample is measured. Also, the temperature difference between two points located in a heat flow path going from the heat reservoir to a reference sample is measured. These two pairs of points are arranged symmetrically. Then, the resulting signals are demodulated, and each signal is divided into an AC component and a low-frequency component. Using these signals, the DSC signal is separated into a heat capacity component and a latent heat component.

18 Claims, 1 Drawing Sheet

THERMAL ANALYSIS INSTRUMENT

BACKGROUND OF THE INVENTION

The present invention relates to a thermal analysis instrument which receives a signal indicating changes in a physical or chemical property of an unknown sample and measures the signal as a function of the unknown sample with respect to temperature or time and, more particularly, to a differential scanning calorimeter (DSC) in which the aforementioned measured signal represents a differential thermal flow between the unknown sample and a reference sample.

U.S. Pat. No. 5,224,775 discloses a method and apparatus for separating a signal obtained from a heat flux DSC into a reversible component and an irreversible component by subjecting linear temperature control of an unknown sample to AC modulation. While ordinary DSC instruments control the temperature of an unknown sample linearly, the direct object of the above-mentioned patent is to divide a DSC signal into a component reflecting a reversible phenomenon and a component reflecting an irreversible phenomenon. For this purpose, the sample temperature is AC modulated, and the obtained signal is demodulated and analyzed.

On the other hand, an AC calorimeter measures minute temperature variations of an unknown sample when minute thermal vibrations are given to the unknown sample, and determines the heat capacity of the unknown sample according to the ratio between the amplitude of the quantity of heat acting as a stimulus and the amplitude of the sample temperature acting as a response. With respect to this AC calorimeter, the following papers are known: Hatta et al., "Studies on Phase Transitions by AC Calorimetry," Japanese Journal of Applied Physics, Vol. 20, No. 11, 1981, pp. 1995–2011; Dixon et al., "A differential AC Calorimeter for Biophysical Studies," Analytical Biochemistry, Vol. 121, pp. 55–61.

A DSC signal becomes a powerful tool when a physical or chemical change of an unknown sample is analyzed in relation to temperature. The DSC signals contain both information about the heat capacity of the unknown sample and information regarding its latent heat. In one method, the specific heat of the unknown sample is found from the DSC signal when no latent heat is present. In another known method, a baseline is drawn empirically to remove the component reflecting the heat capacity of the unknown sample from the DSC signal and thus the latent heat of the unknown sample is correctly found. These and other known methods have enjoyed wide acceptance. However, when the nature of the unknown sample which provides complex data about behaviors of the heat capacity and latent heat is interpreted, possibly empirical elements as described above are involved. Therefore, the nature of the unknown sample is frequently misinterpreted. It is considered that the cause of this drawback arises from the fact that when the DSC instrument itself is producing a signal, the instrument does not separate a component associated with the heat capacity of the unknown sample from a component associated with the latent heat of the unknown sample. It is expected that if the instrument can automatically perform this separation or discrimination, then the aforementioned human errors in interpretation of signals will decrease greatly. This is just the problem that the present invention is intended to solve.

The signal from the AC calorimeter does not contain any component attributed to the latent heat of the unknown sample. With respect to this, the above-cited paper by Hatta et al. describes a technique in conjunction with FIG. 14 of that paper. In particular, results of the DSC are compared with results of the AC calorimeter. A component reflecting the heat capacity of the unknown sample is found from the latter results. A component reflecting the latent heat of the unknown sample is found from the difference between the former results and the latter results. In this case, the same sample is investigated by two kinds of instruments, i.e., the DSC and the AC calorimeter, separately. Then, their results must be compared. In this way, cumbersome operations are needed.

On the other hand, the instrument disclosed in U.S. Pat. No. 5,224,775 is claimed to divide the DSC signal into both a reversible component and an irreversible component. However, a careful consideration of the disclosure in that patent reveals that the technique used to derive the reversible component very closely resembles the method of determination of the heat capacity in the AC calorimeter. Hence, there is the possibility that this technique becomes a means for solving the above-described problem.

However, as disclosed in that patent specification, the instrument is based on the so-called heat flux DSC structure. In particular, the temperature difference between the unknown sample and the reference sample is transformed into the difference between two heat flows, one of which is directed from the unknown sample to a heat reservoir, the other being directed from the reference sample to the heat reservoir. Then, the heat flow difference is measured. In principle, only the temperature difference between the unknown sample and the reference sample is measured.

Hence, the AC heat capacity of the unknown sample cannot be found precisely for the following reason. In order to determine the differential heat capacity between the unknown sample and the reference sample, it is necessary to find the difference between the heat flow amplitude on the side of the unknown sample and the heat flow amplitude on the side of the reference sample. This difference cannot be measured precisely unless these AC heat flows are in phase. In practice, during measurement, if the unknown sample causes a transition such as melting, the phase of the AC heat flow on the side of the unknown sample varies greatly. This makes it impossible to precisely measure the AC heat capacity of the unknown sample.

The inventors of the above-described patent, and others, state that melting of polyethylene terephthalate was measured with an instrument based on the aforementioned patent and that melting of microscopic structures inside the unknown sample and recrystallization were observed, based on the behavior of the separation into a reversible component and an irreversible component. Nonetheless, our experiment has demonstrated that the behavior of separation into the reversible component and the irreversible component can be varied simply by changing the quantity of the reference sample, irrespective of the nature of the unknown sample. Consequently, in measurement of such a system, a signal obtained based on the above patent reflects neither the heat capacity of the unknown sample nor the nature itself of the unknown sample.

This situation can be easily understood from considerations, using the diagram shown in FIG. 2 of the accompanying drawing, bracketed [ ] terms are vectors. Specifically, [Ts] is a vector indicating the AC temperature of an unknown sample. [Tr] is a vector indicating the AC temperature of a reference sample. [dT]=[Ts]−[Tr] is a temperature difference signal which is an archetype of the DSC signal from a heat flux DSC. Generally, if [Ts] and [Tr] differ in sense, we have the relationship $|[T_s]-[T_r]| \neq |[T_s]-[T_r]|$ This can also be understood from the fact that the algebraic difference between the lengths of two sides of the triangle is different from the length of the other one side.

In summary, the instrument disclosed in U.S. Pat. No. 5,224,775 is also unsuccessful in extracting the heat capacity component of the DSC signal by the instrument itself.

SUMMARY OF THE INVENTION

It is an object of the invention to provide an instrument for automatically separating the heat capacity component of a signal and the latent heat component without relying on human intervention, which would have been impossible to achieve by the prior art DSC instrument.

To achieve the above and other objects of the invention, and to solve the above problems, the present invention uses the structure of a conduction type calorimeter. In particular, the heat flow between an unknown sample and a heat reservoir is found from the temperature difference between two points along a heat flow path going from the heat reservoir to the unknown sample. Independently of this, the heat flow between a reference sample and the heat reservoir is found from the temperature difference between two points along a heat flow path going from the heat reservoir to the reference sample. The temperature of the heat reservoir is controlled by a control signal which varies in time according to a ramp function which is modulated by an AC function, in the same way as in U.S. Pat. No. 5,224,775. A heat flow signal on the side of the unknown sample and a heat flow signal on the side of the reference sample are independently demodulated and their respective heat flow amplitudes are found. Then, the difference between them is taken to obtain the amplitude of an excessive heat flow supplied to the unknown sample. This excessive heat flow amplitude is divided by a sample temperature amplitude and an AC angular frequency which are found independently of the excessive heat flow amplitude. Thus, the excessive heat capacity of the unknown sample with respect to the reference sample is obtained, in the same manner as in an AC calorimeter. Furthermore, the excessive heat capacity of the unknown sample is multiplied by the average temperature change rate of the unknown sample so that the excessive heat capacity may be transformed into units of heat flow. This is produced as a heat capacity component signal. Although a DSC signal contains both information concerning the heat capacity of an unknown sample and information concerning the heat capacity, the heat capacity component signal reflects only the former component and represents the baseline of the DSC signal. The heat flow signal on the side of the unknown sample is passed through a low-pass filter. The heat flow signal on the side of the reference sample is processed similarly to derive a low-frequency signal. This low-frequency signal is subtracted from the low-frequency signal from the aforementioned low-pass filter. As a result, a kinetic component signal containing information regarding the latent heat of the unknown sample is obtained.

The structure described above operates in such a way that the instrument itself separates and extracts information concerning the heat capacity of the unknown sample and information concerning the latent heat. The former information has been conventionally unavoidably included in the DSC signal. The latent heat is produced when the unknown sample causes or undergoes a transition or reaction. The resulting heat capacity component signal indicates the position of the correct baseline about the original DSC data. Since the kinetic component signal does not change when the heat capacity of the unknown sample changes, information about enthalpy produced during a transition or reaction can be known precisely.

DESCRIPTION OF THE PREFERRED EMBODIMENTS

Figure 1:
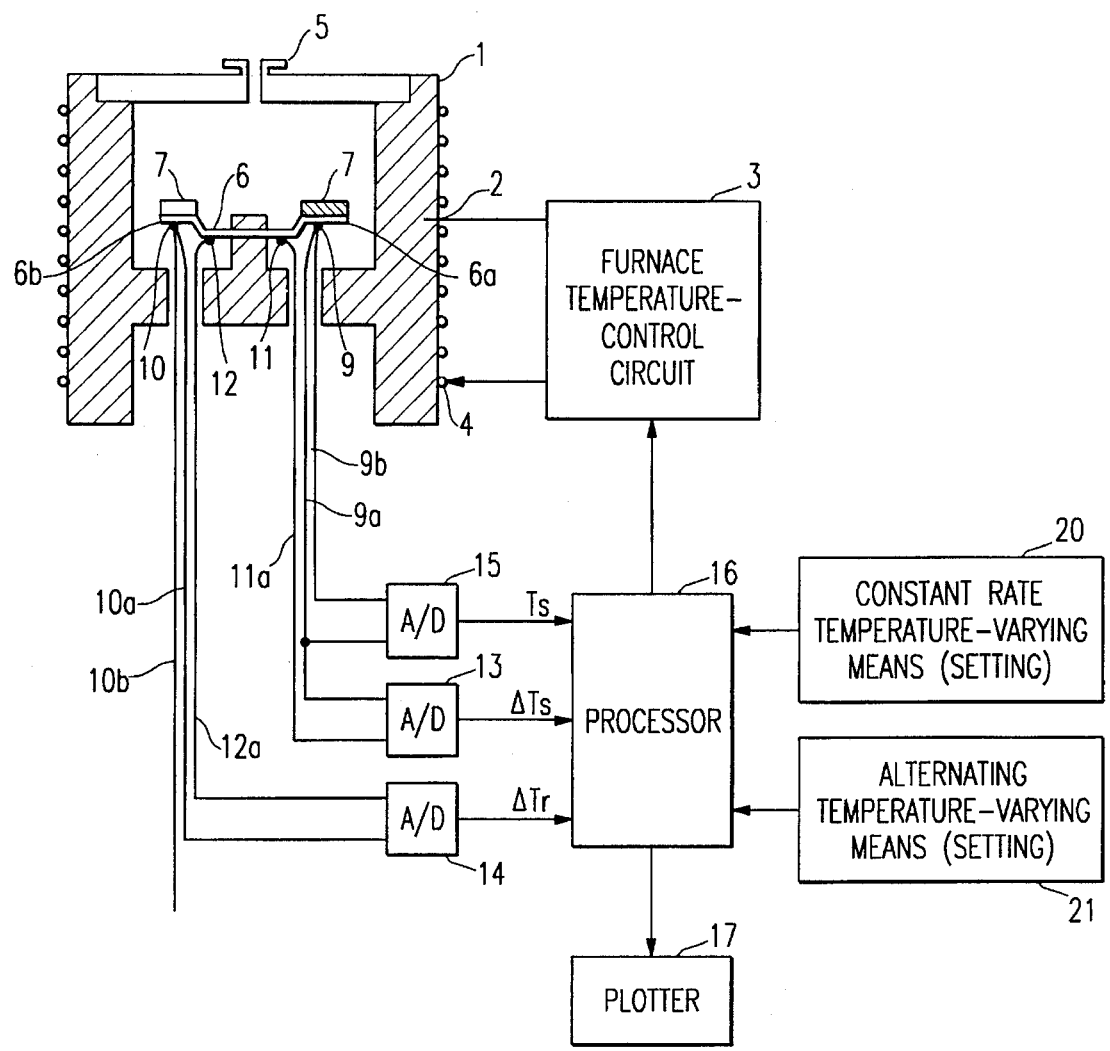
FIG. 1 is partly an elevational cross-sectional view and partly a block circuit diagram illustrating one embodiment of a thermal analysis instrument according to the invention.
Figure 2:
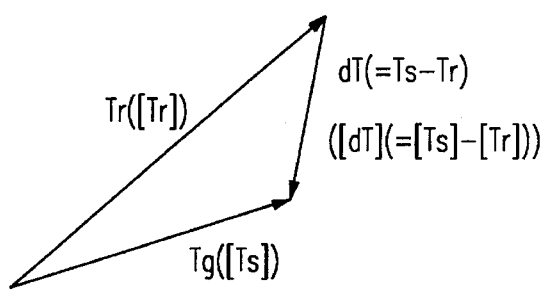
FIG. 2 is a diagram illustrating the operating principle of a prior art instrument.

One embodiment of the present invention is described in detail below with reference to the drawing.

In FIG. 1, a heat reservoir 1 having a substantially H-shaped cross section in a vertical plane is made of, e.g. silver. The temperature (Th) within heat reservoir 1 is measured by a furnace temperature-measuring thermocouple 2. The signal from the thermocouple is fed to a furnace temperature control circuit 3, which in turn supplies electric power to a heater 4 which surrounds reservoir 1 and is enclosed in an insulator. In this way, the temperature of heat reservoir 1 is controlled. For this purpose, a well-known PID (proportional plus integral plus derivative) control action is utilized. In particular, the difference between a temperature indicated by a desired temperature program delivered from a processor 16 and the output temperature from the furnace temperature-measuring thermocouple 2 is produced and subjected to PID operations in the furnace temperature control circuit 3. Output power from the control circuit 3 is supplied to the heater 4.

The desired temperature information produced by processor 16 is dependent on signals provided by setting a constant rate temperature-varying means 20 and an alternating temperature-varying means 21, both connected to processor 16. Appropriate values are set into means 20 and 21 by an operator via a suitable input device, such as a keyboard. Means 20 are set to provide a signal representing a desired constant rate of temperature variation, and means 21 are set to provide an alternating signal representing a desired frequency and peak amplitude of an alternating temperature component which will be superimposed on, or modulate, the constant rate signal.

A heat conduction plate 6 made of constantan (copper-nickel alloy) is mounted at the center of heat reservoir 1 such that the center of plate 6 is fixed inside heat reservoir 1. An unknown sample support portion 6a is formed like a platform at one end of heat conduction plate 6. A reference sample support portion 6b is formed at the other end of heat conduction plate 6. Thus, these two portions 6a and 6b are arranged symmetrically to one another and to the center of heat reservoir 1. An unknown sample loaded in an aluminum container 7 is placed on the unknown sample support portion 6a. A hollow container 7 is placed on the reference sample support portion 6b.

A cover 5 made of, e.g., silver is mounted at the top of heat reservoir 1 to close heat reservoir during operation and is removable to permit containers 7 to be inserted and withdrawn. A chromel-alumel thermocouple 9 (of the K type) comprising a chromel line 9a forming a positive pole and an alumel line 9b forming a negative pole is welded to the underside of the unknown sample support portion 6a to measure the temperature of the unknown sample. Also, a thermocouple 10 comprising a chromel line 10a forming a positive pole and an alumel line 10b forming a negative pole is welded to the underside of the reference sample support portion 6b to retain the symmetry of the unknown sample support portion 6a and the reference sample support portion 6b. In practice, however, the thermocouple 10 is not connected to measure any temperature.

A chromel line 11a is welded to a given point 11 located between unknown sample support portion 6a and the fixed point on heat conduction plate 6 at which plate 6 is fixed to heat reservoir 1. The chromel line 11a cooperates with the material, e.g. constantan, of the heat conduction plate 6, to form a thermocouple 11. A chromel line 12a is welded to a given point 12 located between reference sample support portion 6b and the fixed point on heat conduction plate 6 at which plate 6 is fixed to heat reservoir 1. The chromel lines 11a and 12a are arranged symmetrically to the center of plate 6 and reservoir 1. The chromel line 12a cooperates with the material, constantan, of heat conduction plate 6, to form a thermocouple 12.

A voltage developed between chromel lines 9a and 11a indicates the temperature difference ($\Delta T_s$) between points 9 and 11, which reflects the electromotive force produced by the chromel-constantan thermocouple. This voltage is applied to an analog-to-digital converter 13, where the voltage is converted into a digital signal. Then, the signal is supplied to the processor 16, where the signal is processed. Similarly, with respect to a temperature difference ($\Delta T_r$) between the points 10 and 12, a voltage generated between the chromel lines 10a and 12a is fed to an analog-to-digital converter 14, where the voltage is converted into a digital form. The signal from the converter is supplied to the processor 16, where the signal is processed. A voltage developed between chromel line 9a and alumel line 9b indicates the temperature at point 9 located at the underside of unknown sample support portion 6a, the temperature reflecting the electromotive force produced by the chromel-alumel thermocouple. This voltage is converted into digital form by an analog-to-digital converter 15 and then sent as a signal $T_s$ indicative of the temperature of the unknown sample to the processor 16, where the signal is processed. The processor 16 sends to furnace temperature control circuit 3 control information which is a function of a program designating a desired temperature to which the temperature of heat reservoir 1 should be controlled. In addition, processor 16 sends the signals received from A/D converters 13, 14 and 15 to a recorder means such as a plotter 17 either directly or through the intermediary of a mathematical processing means which mathematically processes the signals in a given manner.

In the operation of the present instrument, the operator first enters into constant rate temperature-varying means 20, by any suitable input means, a temperature rise speed B (°C./min) increasing linearly with respect to time, and into alternating temperature-varying means 21 an AC modulation frequency f (Hz), and an AC modulation amplitude A (°C.). These parameters are then delivered to processor 16. The processor 16, which is triggered by instructions from an operator for starting a measurement, produces a temperature program function $T_p(t)$ with respect to time t(s) to furnace temperature control circuit 3, the function $T_p$ taking the form:

$$T_p(t) = Th(0) + (B/60) \cdot t - A \cdot \sin(\pi \cdot f \cdot t)$$

where Th(0) is the temperature of heat reservoir 1 when the measurement is initiated.

The furnace temperature control circuit 3 supplies an output voltage to heater 4, the output voltage being PID controlled according to the difference between $T_p$ and Th. Thus, the temperature Th of heat reservoir 1 is maintained coincident with $T_p$. As a result, the profile of the temperature of heat reservoir 1 is substantially identical with the temperature program function $T_p$ (t) specified by the operator.

At this time, heat is conducted to unknown sample support portion 6a and to reference sample support portion 6b from the interior of heat reservoir 1 via heat conduction plate 6 according to changes in the temperature of heat reservoir 1, indicated by the equation of heat conduction. The amount of heat supplied reflects the nature of the unknown sample. A heat flow $-q_s$ (mW) indicating the amount of heat supplied to the unknown sample per second is obtained by dividing the temperature difference between two points along the heat flow path by the heat resistance between the two points according to the thermal version of Ohm's law. Therefore, the heat flow is derived by dividing the temperature difference signal $\Delta T_s$ (°C.) by the heat resistance value R (mW/°C.) between the points 9 and 11 at heat conduction plate 6. That is, $$q_s(t) = \Delta T_s(t)/R.$$

If the heat flow to the symmetrical reference sample is given by $-q_r$ (mW), then it can be expressed in the same way as the heat flow to the unknown sample, i.e., $$q_r(t) = \Delta T_r(t)/R.$$

If the operator sets the AC modulation amplitude A to 0, ordinary DSC data is obtained by sending a differential heat flow signal $q_s - q_r$ from processor 16 to plotter 17 and making a record of this signal with respect to the unknown sample temperature $T_s$.

On the other hand, where $A \neq 0$, each of the signals $T_s$, $q_s$ and $q_r$ takes a form of its average low-frequency signal component on which a signal component having the periodicity of frequency f is superimposed. In this case, signals equivalent to ordinary DSC signals can be obtained by using, instead of the signals $T_s$, $q_s$, and $q_r$, their average values "$T_s$", "$q_s$" and "$q_r$", taken over their respective single periods (1/f) (i.e., the average output value of values taken during two half periods, respectively, before and after a certain temperature) and plotting differential heat flow signal "$q_s$"–"$q_r$" against "$T_s$". This "$q_s$"–"$q_r$" signal is produced as a total heat flow component signal from processor 16 to plotter 17.

Processor 16 filters output signals from converter 13, which constitutes first temperature difference measuring means, output signals from converter 14, which constitutes second temperature difference measuring means, and converter 15, which constitutes sample temperature measuring means, for dividing each signal into an AC component corresponding to the frequency of the alternating component, the AC component having an AC amplitude, and a low frequency component independent of that frequency.

The total heat flow component signal produced by processor 16 is thus a function of the difference between the low frequency component of the output signal from converter 13 and the low frequency component of the output signal from converter 14.

The processor 16 finds the amplitudes of the AC components of the signals $T_s$, $q_s$, and $q_r$ by the following discrete Fourier transform method.

$$\text{Amp}(Ts(t)) = \left| 2f \cdot \int_{-1/2f}^{+1/2f} (Ts(t+t') - \overline{Ts}(t+t')) \cdot \exp(-i \cdot 2\pi ft')dt' \right| \quad (1)$$

$$\text{Amp}(qs(t)) = \left| 2f \cdot \int_{-1/2f}^{+1/2f} (qs(t+t') - \overline{qs}(t+t')) \cdot \exp(-i \cdot 2\pi ft')dt' \right| \quad (2)$$

$$\text{Amp}(qr(t)) = \left| 2f \cdot \int_{-1/2f}^{+1/2f} (qr(t+t') - \overline{qr}(t+t')) \cdot \exp(-i \cdot 2\pi ft')dt' \right| \quad (3)$$

where Amp ( ) indicates the AC amplitude of the signal inside the parentheses, | | indicates the absolute value of the value enclosed thereby, exp ( ) indicates an exponential function, or a function expressing the index of the value included in the parentheses, i is the imaginary unit $(-1)^{1/2}$, and $\pi$ is the ratio of the circumference of a circle to its diameter.

By using a calculation method similar to the method used in AC calorimeters, the difference $\Delta C_p$ (mJ/°C.) in AC heat capacity between the unknown sample and the reference sample is found from the AC amplitudes of the signals as follows.

$$\Delta C_p = \frac{\text{Amp}(qs) - \text{Amp}(qr)}{2\pi f \cdot \text{Amp}(Ts)} \quad (4)$$

Especially, where the operator performs a measurement in such a way that the container for the reference sample is empty the above $\Delta C_p$ indicates the AC heat capacity of the unknown sample itself. As is well known in the field of AC calorimeters, the AC heat capacity of an unknown sample does not indicate a latent heat associated with a transition caused by the unknown sample. The above $\Delta C_p$ signal is also supplied to plotter 17 from processor 16.

Thus, processor 16 derives an indication of the heat capacity of the unknown sample according to a ratio of a difference between the AC amplitude of the output signal from converter 13 and the AC amplitude of the output signal from converter 14 to the AC amplitude of the output from converter 15.

The above differential heat capacity $\Delta C_p$ can be transformed into units of heat flow which can be compared with the above-described total heat flow component signal, by multiplying $\Delta C_p$ by the average temperature rise rate d"$T_s$"/dt of the unknown sample. That is, the heat capacity component ($C_p$ component) is defined by the following equation:

$$C_p\text{component}(mW) = -\Delta C_p(mJ/°C.) \times \frac{d\overline{Ts}}{dt} \quad (°C./s) \quad (5)$$

Thus, since $\Delta C_p$ constitutes an indication of the heat capacity of the unknown sample itself, processor 16 provides an indication in units of heat flow as a signal, $C_p$ component, indicative of the heat capacity component based on $\Delta C_p$ multiplied by the average temperature change rate of the low frequency component of the output signal from converter 15.

The heat capacity component obtained in this way is not affected by the latent heat produced by a transition or reaction produced by or in the unknown sample and, therefore, this component acts to give the baseline when the latent heat is found from the DSC signal. This component is calculated by processor 16 and sent to plotter 17. The difference between the above-described total heat flow component signal "$q_s$"–"$q_r$" and the above heat capacity component reflects only the latent heat component. This is defined as the kinetic component signal according to the following equation:

kinetic component (mW)=total heat flow component (mW)–total heat capacity component (mW).

Thus, the kinetic component signal is based on a difference between the value of the total heat flow component signal and the value of the signal indicative of a component of the heat capacity.

The kinetic component obtained in this way is also supplied to plotter 17 from processor 16.

Various signals including the total heat flow component signal, the heat capacity component signal, and the kinetic component signal delivered from processor 16 as described above are recorded on plotter 17 with respect to either the average temperature "$T_s$" of the unknown sample, taken over one period, or time.

In the present example, thermocouples are used in measuring the temperature differences $\Delta T_s$ and $\Delta T_r$. Commercially available thermomodules and platinum resistors can also be employed.

Of course, if a refrigerant such as liquid nitrogen, vaporized refrigerant, or other cooling means is used in conjunction with heater 4, then the response of the control over the temperature in heat reservoir 1 is effectively improved.

In order to investigate the thermal property of an unknown sample, the temperature difference $\Delta T_s$ between thermocouple junction 9 on the side of the unknown sample and thermocouple junction 11 connected to heat conduction plate 6 is found while measuring the temperature difference $\Delta T_r$ between thermocouple junction 10 on reference sample support portion 6b and the thermocouple junction 12 on heat conduction plate 6. The difference between these differences $\Delta T_r$ and $\Delta T_s$ is found. Thus, the heat capacity and the latent heat of the unknown sample are determined. If the temperature elevation conditions and reference sample support portion 6b remain the same, then the change in $\Delta T_r$ with respect to time or temperature is maintained constant. Consequently, the above-described measurement object can be accomplished simply by measuring the temperature difference $\Delta T_s$.

As described thus far, in the present invention, a heat flux type DSC is so improved that a heat flow on the side of an unknown sample and a heat flow on the side of a reference sample can be measured independently and that the temperature of a heat reservoir can be controlled according to a ramp function modulated with an alternating sinusoidal wave. In consequence, DSC measurements can be performed. Additionally, the AC heat capacity of the unknown sample can be measured with high accuracy. Also, only information about the heat capacity can be extracted from a DSC signal which inevitably includes information about the latent heat, as well as information about the heat capacity. Hence, the baseline of the DSC signal becomes apparent. The latent heat of the unknown sample can be measured accurately. Further, with respect to a complex DSC thermogram, the instrument itself judges whether a change in the DSC signal is caused by a change in the heat capacity of the unknown sample or by a latent heat. Therefore, when data is interpreted, the possibility of human errors is reduced drastically.

This application relates to subject matter disclosed in Japanese Application number 5-238408, filed on Sep. 24, 1993, the disclosure of which is incorporated herein by reference.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed:

1. A thermal analysis instrument comprising:

a heat reservoir made of a thermal conducting material and having a center;

temperature-varying means coupled to said heat reservoir for varying temperature of said heat reservoir according to a function of time, which function has a linear component that varies at a constant rate and an alternating component that has a given frequency and amplitude and modulates the linear component;

a thermally conductive support member disposed in said heat reservoir for supporting an unknown sample and a reference sample symmetrically with respect to said center of said reservoir, said thermally conductive support member forming heat flow paths;

first temperature difference-measuring means thermally coupled to said thermally conductive support member for measuring a heat flow in one of the heat flow paths between a given point close to the unknown sample and a first fixed point as a temperature difference, the first fixed point being spaced from the location of the unknown sample;

second temperature difference-measuring means thermally coupled to said thermally conductive support member for measuring a heat flow in another one of the heat flow paths between a given point close to the reference sample and a second fixed point as a temperature difference, the second fixed point being spaced from the location of the reference sample, said first and second temperature difference-measuring means being formed and located symmetrically with respect to said center of said reservoir;

sample temperature-measuring means thermally coupled to said support member for measuring temperature at a point that is located on said support member and is close to the unknown sample; and recording means coupled to said first and second temperature difference-measuring means and said sample temperature-measuring means for recording outputs from said first temperature difference-measuring means, said second temperature difference-measuring means, and said sample temperature measuring means as a function of one of time and temperature of the unknown sample.

2. The thermal analysis instrument of claim 1, wherein the alternating component is a sinusoidal wave.

3. The thermal analysis instrument of claim 1, wherein a difference between the output from said first temperature difference-measuring means and the output from said second temperature difference-measuring means is used to provide a signal for differential scanning calorimetry.

4. The thermal analysis instrument of claim 1, further comprising processor means for filtering output signals from said first temperature difference-measuring means, said second temperature difference-measuring means, and said sample temperature-measuring means, whereby each signal is divided into an AC component corresponding to the frequency of the alternating component, the AC component having an AC amplitude, and a low-frequency component independent of that frequency.

5. The thermal analysis instrument of claim 4, wherein said processor means derive an indication of a heat capacity of the unknown sample according to a ratio of a difference between the AC amplitude of the output signal from said first temperature difference-measuring means and the AC amplitude of the output signal from said second temperature difference-measuring means to the AC amplitude of the output from said sample temperature-measuring means.

6. The thermal analysis instrument of claim 4, wherein said processor means produce a total heat flow component signal which is a function of a difference between the low-frequency component of the output signal from said first temperature difference-measuring means and the low-frequency component of the output signal from said second temperature difference-measuring means.

7. The thermal analysis instrument of claim 6, wherein said processor means derive an indication of a heat capacity of the unknown sample according to a ratio of a difference between the AC amplitude of the output signal from said first temperature difference-measuring means and the AC amplitude of the output signal from said second temperature difference-measuring means to the AC amplitude of the output from said sample temperature-measuring means.

8. The thermal analysis instrument of claim 7, wherein said processor means derive an indication of heat flow delivered as a signal indicative of a component of the heat capacity based on the indication of heat capacity of the unknown sample derived by said processor means multiplied by an average change rate of the low-frequency component of the output signal from said sample temperature-measuring means.

9. The thermal analysis instrument of claim 8, wherein said processor means further derive a kinetic component signal based on a difference between the value of the total heat flow component signal and the value of the signal indicative of a component of the heat capacity.

10. A thermal analysis method comprising:

providing a heat reservoir made of a thermal conducting material and having a center, and disposing a thermally conductive support member in the heat reservoir for supporting an unknown sample and a reference sample symmetrically with respect to the center of the reservoir, the thermally conductive support member forming heat flow paths;

varying the temperature in the heat reservoir according to a function of time, which function has a linear component that varies at a constant rate and an alternating component that has a given frequency and amplitude and modulates the linear component;

measuring a heat flow in a first one of the heat flow paths between a given point close to the unknown sample and a first fixed point as a first temperature difference, the first fixed point being spaced from the location of the unknown sample;

measuring a heat flow in a second one of the heat flow paths between a given point close to the reference sample and a second fixed point as a second temperature difference, the second fixed point being spaced from the location of the reference sample, the heat flows in the first and second heat flow paths being measured at locations which are symmetrical with respect to the center of the reservoir;

measuring the unknown sample temperature at a point that is located on the support member and is close to the unknown sample; and recording the first temperature difference, the second temperature difference and the unknown sample temperature as a function of one of time and temperature of the unknown sample.

11. The method of claim 10, wherein the alternating component is a sinusoidal wave.

12. The method of claim 10, wherein a difference between the first temperature difference and the second temperature difference is used to provide a signal for differential scanning calorimetry.

13. The method of claim 10, further comprising filtering signals representing the first temperature difference, the second temperature difference and the unknown sample temperature, whereby each signal is divided into an AC component corresponding to the frequency of the alternating component, the AC component having an AC amplitude, and a low-frequency component independent of that frequency.

14. The method of claim 13, further comprising deriving an indication of a heat capacity of the unknown sample according to a ratio of a difference between the AC amplitude of the signal representing the first temperature difference and the AC amplitude of the signal representing the second temperature difference to the AC amplitude of the signal representing the unknown sample temperature.

15. The method of claim 13, further comprising producing a total heat flow component signal which is a function of a difference between the low-frequency component of the signal representing the first temperature difference and the low-frequency component of the signal representing the second temperature difference.

16. The method of claim 15, further comprising deriving an indication of a heat capacity of the unknown sample according to a ratio of a difference between the AC amplitude of the signal representing the first temperature difference and the AC amplitude of the signal representing the second temperature difference to the AC amplitude of the signal representing the unknown sample temperature.

17. The method of claim 16, further comprising deriving an indication of heat flow delivered as a signal indicative of a component of the heat capacity based on the derived indication of heat capacity of the unknown sample multiplied by an average change rate of the low-frequency component of the signal representing the unknown sample temperature.

18. The method of claim 17, further comprising deriving a kinetic component signal based on a difference between the value of the total heat flow component signal and the value of the signal indicative of a component of the heat capacity.

* * * * *